United States Patent [19]

Nishiyama et al.

[11] 4,230,481
[45] Oct. 28, 1980

[54] PYRAZOLE DERIVATIVES USEFUL AS A HERBICIDAL COMPONENT

[75] Inventors: Ryuzo Nishiyama, Takatsuki; Fumio Kimura, Kusatsu; Takahiro Haga, Kusatsu; Nobuyuki Sakashita, Kusatsu; Tetsuji Nishikawa, Kusatsu, all of Japan

[73] Assignee: Ishihara Sangyo Kaisha Limited, Osaka, Japan

[21] Appl. No.: 929,564

[22] Filed: Jul. 31, 1978

[30] Foreign Application Priority Data

Aug. 12, 1977 [JP] Japan ................................. 52-96110
Nov. 10, 1977 [JP] Japan ................................. 52-134072

[51] Int. Cl.³ .................... A01N 43/56; C07D 231/10
[52] U.S. Cl. ......................................... 71/92; 548/377; 71/90
[58] Field of Search ............................. 71/92; 548/377

[56] References Cited

U.S. PATENT DOCUMENTS

| | | | |
|---|---|---|---|
| 3,869,274 | 3/1975 | Crovetti et al. | 548/377 |
| 4,008,249 | 2/1977 | Fischer et al. | 71/92 |
| 4,063,925 | 12/1977 | Konotsune et al. | 71/92 |

FOREIGN PATENT DOCUMENTS

| | | | |
|---|---|---|---|
| 50-106738 | 3/1975 | Japan | 71/92 |
| 1242810 | 8/1971 | United Kingdom | 71/92 |

*Primary Examiner*—Glennon H. Hollrah
*Attorney, Agent, or Firm*—Oblon, Fisher, Spivak, McClelland & Maier

[57] ABSTRACT

A pyrazole derivative having the formula (I):

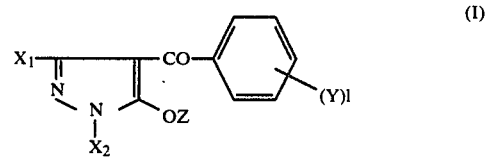

wherein $X_1$ and $X_2$ are respectively a ($C_1$-$C_4$) alkyl group, Y is a halogen atom, nitro group, acetyl group, cyano group, or a phenoxy group which may be substituted with one or more halogen atoms, l is an integer of 1 to 3, and Z is a ($C_1$-$C_4$) alkyl group, a ($C_2$-$C_4$) alkenyl group, a ($C_2$-$C_4$) alkynyl group, acetylmethyl group, an aralkyl group in which the aryl moiety thereof may be substituted with one or more nitro groups, a phenacyl group in which the phenyl moiety thereof may be substituted with one or more halogen atoms, one or more nitro groups, one or more ($C_1$-$C_4$) alkyl groups, one or more ($C_1$-$C_4$) alkoxy groups, one or more ($C_1$-$C_4$) alkylthio groups, acetyl group, acetylamino group, cyano group, methylsulfonyl group, phenoxy group or phenyl group; a dinitrophenyl group, or a thenoylmethyl group in which the cyclic moiety thereof may be substituted with one or more halogen atoms or one or more ($C_1$-$C_4$) alkyl groups, which is useful as a herbicidal component in paddy fields.

12 Claims, No Drawings

PYRAZOLE DERIVATIVES USEFUL AS A HERBICIDAL COMPONENT

BACKGROUND OF THE INVENTION

1. Field of the Invention

This invention relates to a novel compound useful as a herbicide for agriculture and horticulture, to a herbicidal composition containing the compound, and to a process for preparing the compound.

2. Description of the Prior Arts

It has been developed to control annual weeds such as barnyard grass (*Echinochloa crus-galli* BEAUV) and toothcup (*Rotala indica* KOEHNE) by a treatment of a herbicide at the initial stage of growth of rice plants. However, it has not been enough to control perennial weeds such as bulrush (*Scirpus Juncoides* var. Hotarui), chufa (*Cyperus microiria* STEUD), water plantain (*Sagittaria trifolia* L) and arrowhead (*Sagittaria pygmaea* MIQ), whereby such perennial weeds have grown thick to prevent the growth of rice plants. Thus, the control of these perennial weeds has been required. It has been proposed to use 4-benzoyl-5-hydroxypyrazole derivatives as herbicides being active against these perennial weeds in U.S. Pat. No. 4,063,925.

The inventors have studied on novel compounds of 4-benzoyl-5-hydroxypyrazole derivatives having hydrocarbon moiety bonded by an ether bond at 5-position of the pyrazole ring and have found that the specific novel compounds impart excellent herbicidal effect to these perennial weeds without any phytotoxicity to rice plants and impart superior herbicidal effect to the annual weeds at the initial stage of growth to the known 4-benzoyl-5-hydroxypyrazole derivatives.

SUMMARY OF THE INVENTION

It is an object of the present invention to provide a novel pyrazole derivative having the formula (I):

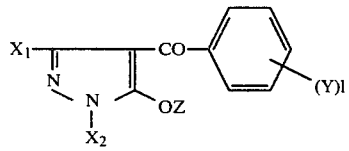

wherein $X_1$ and $X_2$ are respectively a $(C_1-C_4)$ alkyl group, Y is a halogen atom, nitro group, acetyl group, cyano group, or a phenoxy group which may be substituted with one or more halogen atoms, l is an integer of 1 to 3, and Z is a $(C_1-C_4)$ alkyl group, a $(C_2-C_4)$ alkenyl group, a $(C_2-C_4)$ alkynyl group, acetylmethyl group, an aralkyl group in which the aryl moiety thereof may be substituted with one or more nitro groups; a phenacyl group in which the phenyl moiety thereof may be substituted with one or more halogen atoms, one or more nitro groups, one or more $(C_1-C_4)$ alkyl groups, one or more $(C_1-C_4)$ alkoxy groups, one or more $(C_1-C_4)$ alkylthio groups, acetyl group, acetylamino group, cyano group, methylsulfonyl group, phenoxy group or phenyl group; a dinitrophenyl group, or a thenoylmethyl group in which the cyclic moiety thereof may be substituted with one or more halogen atoms or one or more $(C_1-C_4)$ alkyl groups.

It is another object of the present invention to provide a herbicidal composition comprising a herbicidally effective amount of at least one compound of the formula (I) as an active ingredient and an agriculturally acceptable adjuvant.

It is the other object of the present invention to provide a process for preparing novel pyrazole derivatives.

DETAILED DESCRIPTION OF THE PREFERRED EMBODIMENTS

In the definition of the above-mentioned formula (I), $(C_1-C_4)$ alkyl groups include methyl, ethyl, n-propyl, isopropyl, n-butyl, sec-butyl, isobutyl and tert-butyl groups; $(C_2-C_4)$ alkenyl groups include allyl, 2-butenyl and 2-methyl-2-propenyl groups; $(C_2-C_4)$ alkynyl groups include 2-propynyl; $(C_1-C_4)$ alkoxy groups include methoxy and ethoxy groups; $(C_1-C_4)$ alkylthio groups include methylthio and ethylthio groups; aralkyl groups include benzyl and phenethyl groups; and halogen atoms include fluorine, chlorine, bromine and iodine.

When $(Y)l$ are plural substituents or Z has plural substituents, these substituents can be the same or different each other.

The pyrazole derivatives having the formula (I) are classified to the following groups.

A.

$X_1$, $X_2$: $(C_1-C_4)$ alkyl group

Y: halogen atom, nitro group, acetyl group, cyano group.

l: 1, 2

Z: $(C_1-C_4)$ alkyl group; acetylmethyl group; $(C_2-C_4)$ alkenyl group; $(C_2-C_4)$ alkynyl group; aralkyl group in which the aryl moiety thereof may be substituted with a nitro group; phenacyl group in which the phenyl moiety thereof may be substituted with one or more halogen atoms, one or more nitro groups, cyano group, or methylsulfonyl group; dinitrophenyl group

B.

$X_1$, $X_2$: $(C_1-C_4)$ alkyl group

Y: halogen atom, nitro group, cyano group l: 1, 2

Z: phenacyl group in which the phenyl moiety thereof is substituted with one or more $(C_1-C_4)$ alkyl groups, or one or more $(C_1-C_4)$ alkoxy groups From the viewpoints of herbicidal activity, the pyrazole derivatives having the formula (II) are superior among the pyrazole derivatives having the formula (I).

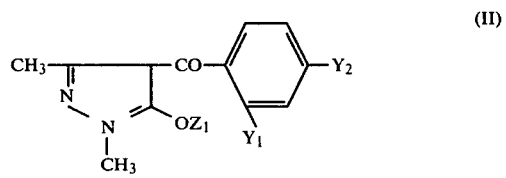

wherein $Y_1$ and $Y_2$ are respectively chlorine atom or nitro group, and $Z_1$ is (1) a phenacyl group in which the phenyl moiety thereof may be substituted with one or more halogen atoms, one or more nitro groups, one or more $(C_1-C_4)$ alkyl groups, one or more $(C_1-C_4)$ alkoxy groups, one or more $(C_1-C_4)$ alkylthio groups, acetyl group, acetylamino group, cyano group, methylsulfonyl group, phenoxy group or phenyl group; or (2) a dinitrophenyl group; or (3) a thenoylmethyl group in which the cyclic moiety thereof may be substituted with one or more halogen atoms or one or more (C₁-C₄) alkyl groups.

It is most preferable to select the pyrazole derivatives having the formula (II) wherein $Y_1$ and $Y_2$ are respectively chlorine atom, and $Z_1$ is a phenacyl group in which the phenyl moiety thereof may be substituted with one or two chlorine atoms, or one or two methyl groups.

The pyrazole derivatives having the formula (I) can be produced by the following process.

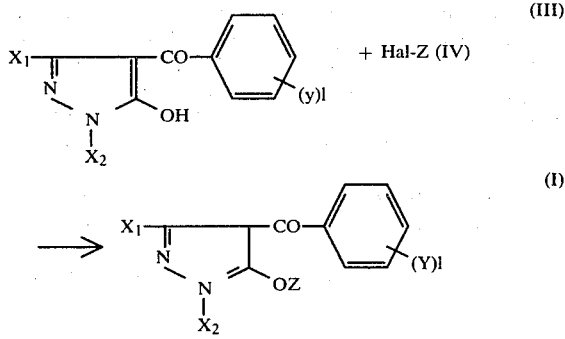

In the reaction formula, $X_1$, $X_2$, Y and l are defined above and Hal is a halogen atom such as fluorine, chlorine and bromine.

In the reaction, it is advantageous to use a solvent such as aprotic-polar solvents e.g. acetone, methyl ethyl ketone, methyl isobutyl ketone, dimethyl sulfoxide, dimethylacetamide, dimethylformamide, N-methylpyrrolidone, hexamethylphosphoramide and sulfolane; alcohol solvents e.g. methanol, ethanol, and isopropanol. The solvent is usually used in a range of 3 to 20 wt. parts preferably 5 to 10 wt. parts per 1 wt. part of the compound (III).

It is most preferable to use the ketone solvents such as methyl ethyl ketone and the alcohol solvents such as methanol and ethanol.

It is advantageous to use alkali-metal hydroxides such as sodium hydroxide and potassium hydroxide or alkali-metal carbonates such as sodium carbonate and potassium carbonate as the alkaline compound. The alkaline compound is usually used in a range of 1 to 2 mol preferably 1.1 to 1.5 mol per 1 mol of the compound (III).

It is most preferable to use sodium hydroxide as the alkali-metal hydroxide. When sodium hydroxide is used, it is preferable to use an alcohol as the solvent.

The reactivity can be improved by using a cuprous halide such as cuprous iodide and cuprous fluoride as a catalyst.

In the reaction, the reaction temperature is usually in a range of 1 to 5 hours preferably 1 to 3 hours and the reaction temperature is in a range of 50° C. to a reflux temperature (based on a boiling point of the solvent). Certain examples of preparations of the compounds of the present invention will be illustrated.

PREPARATION 1

1,3-Dimethyl-4-(2,4-dichlorobenzoyl)-5-(2,4-dinitrophenoxy) pyrazole

In a four necked flask, 1.43 g of 1,3-dimethyl-4-(2,4-dichlorobenzoyl)-5-hydroxypyrazole was dissolved in 15 ml of methyl ethyl ketone and 1.38 g of anhydrous potassium carbonate was added to the solution and 0.93 g of 2,4-dinitrophenylfluoride was added dropwise to the mixture under stirring. After the addition, the reaction was carried out for 3 hours under refluxing. The reaction mixture was filtered and methyl ethyl ketone was distilled off to obtain the precipitate of the reaction product. The precipitate was dissolved in methylene chloride and the solution was mixed with a saturated aqueous solution of sodium bicarbonate. The organic phase was separated and methylene chloride was distilled off to obtain the solid product. The solid product was washed with benzene to obtain 1.58 g of 1,3-dimethyl-4-(2,4-dichlorobenzoyl)-5-(2,4-dinitrophenoxy) pyrazole having a melting point of 190° to 192° C.

PREPARATION 2

1,3-Dimethyl-4-(2,4-dichlorobenzoyl)-5-propargyloxy pyrazole

In accordance with the process of Preparation 1 except using 0.71 g of propargyl bromide instead of 0.93 g of 2,4-dinitrophenyl fluoride, the process of the reaction and the purification was repeated to obtain 0.93 g of 1,3-dimethyl-4-(2,4-dichlorobenzoyl)-5-propargyloxy pyrazole having a refractive index of $n_D^{25}$ 1.585.

PREPARATION 3

1,3-Dimethyl-4-(2,4-dichlorobenzoyl)-5-(4-chlorobenzoylmethoxy) pyrazole

In accordance with the process of Preparation 1 except using 1.0 g of p-chlorophenacyl bromide instead of 0.93 g of 2,4-dinitrophenyl fluoride, the process of the reaction and purification was repeated to obtain 1.72 g of brown semi-solid product of 1,3-dimethyl-4-(2,4-dichlorobenzoyl)-5-(4-chlorobenzoylmethoxy) pyrazole.

PREPARATION 4

1,3-Dimethyl-4-(2-chloro-4-nitrobenzoyl)-5-methoxy pyrazole

In a four necked flask, 1.4 g of 1,3-dimethyl-4-(2-chloro-4-nitrobenzoyl)-5-hydroxypyrazole was dissolved in 10 ml of ethyl ether. The solution was cooled with ice-water and an ether solution of diazomethane was added and the reaction was carried out until ceasing nitrogen gas. Diazomethane and ether were distilled off from the reaction mixture to obtain the precipitate of the reaction product. The precipitate was dissolved in methylene chloride. The solution was mixed with a saturated aqueous solution of sodium bicarbonate. The organic phase was separated and methylene chloride was distilled off to obtain a solid product. The solid product was dissolved in toluene and adsorbed on a silica gel column and eluted with methylene chloride to obtain 0.8 g of 1,3-dimethyl-4-(2-chloro-4-nitrobenzoyl)-5-methoxy pyrazole having a melting point of 97° to 98° C.

PREPARATION 5

1,3-Dimethyl-4-(2,4-dichlorobenzoyl)-5-(4-methylbenzoylmethoxy) pyrazole

In a four necked flask, 2 g of 1,3-dimethyl-4-(2,4-dichlorobenzoyl)-5-hydroxy pyrazole was dissolved in 35 ml of methyl ethyl ketone, and 2 g of anhydrous potassium carbonate was added to the solution and 1.4 g of 4-methylphenacyl bromide was added dropwise to the mixture under stirring. The reaction was carried out for 2 hours under refluxing. The reaction mixture in the flask was cooled and filtered and methyl ethyl ketone was distilled off to obtain the precipitate of the reaction product. The precipitate was dissolved in methylene chloride and the solution was sequentially washed with water, an aqueous solution of sodium bicarbonate and water, and after drying over anhydrous sodium sulfate, methylene chloride was distilled off from the solution to obtain a crude product. The product was separated by a silica gel column with developing solvent ($CH_2Cl_2$: 99.5% $C_2H_5OH$ = 100: 3) to obtain 1.87 g of brown oily product of 1,3-dimethyl-4-(2,4-dichlorobenzoyl)-5-(4-methyl benzoylmethoxy) pyrazole.

PREPARATION 6

1,3-Dimethyl-4-(2,4-dichlorobenzoyl)-5-(benzoylmethoxy) pyrazole

In accordance with the process of Preparation 1 except using 0.92 g of phenacyl bromide instead of 0.93 g of 2,4-dinitrophenyl fluoride, the process of the reaction and the purification was repeated to obtain 1.32 g of 1,3-dimethyl-4-(2,4-dichlorobenzoyl)-5-(benzoylmethoxy) pyrazole having a melting point of 102° to 104° C.

Typical examples of the pyrazole derivatives of the formula (I) of the present invention are given below:

Table 1

| Compound No. | $X_1$ | $X_2$ | $(Y)_l$ | Z | Physical constant |
|---|---|---|---|---|---|
| 1 | $CH_3$ | $CH_3$ | 2-Br | —$CH_3$ | |
| 2 | " | " | 2-$COCH_3$ | " | |
| 3 | " | " | 4-$NO_2$ | " | mp 121°–124° C. |
| 4 | " | " | 4-CN | " | |
| 5 | " | " | 2,4-$Cl_2$ | " | mp 145°–150° C. |
| 6 | " | " | 2-Cl, 4-$NO_2$ | " | mp 97°–98° C. |
| 7 | " | " | 2-$NO_2$, 4-Cl | " | |
| 8 | " | " | 2-$COCH_3$ | —$CH_2$—CH=$CH_2$ | |
| 9 | " | " | 4-Cl | " | mp 212°–215° C. |
| 10 | " | " | 4-CN | " | mp 69°–71° C. |
| 11 | " | " | 2,4-$Cl_2$ | " | $n_D^{25}$ 1.574 |
| 12 | " | " | " | —$CH_2$CH=$CHCH_3$ | $n_D^{25}$ 1.581 |
| 13 | " | " | " | —$CH_2$C=$CH_2$ \| $CH_3$ | mp 49°–53° C. |
| 14 | " | " | 3-$NO_2$ | —$CH_2$C≡CH | $n_D^{25}$ 1.564 |
| 15 | " | " | 2,4,-$Cl_2$ | " | $n_D^{25}$ 1.585 |
| 16 | " | " | 2-Cl, 4-$NO_2$ | " | mp 104°–105° C. |
| 17 | " | " | 2,4-$Cl_2$ | —$CH_2COCH_3$ | brown oil |
| 18 | " | " | 2-CL, 4-$NO_2$ | " | mp 94°–96° C. |
| 19 | " | " | 2,4-$Cl_2$ | —$CH_2CH_2$— 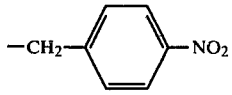 | $n_D^{25}$ 1.587 |
| 20 | " | " | 2-Cl, 4-$NO_2$ | " | mp 163°–165° C. |
| 21 | " | " | 2-$COCH_3$ | —$CH_2$— 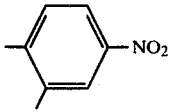 —$NO_2$ | |
| 22 | " | " | 2-$NO_2$ | " | |
| 23 | " | " | 4-$NO_2$ | " | mp 225°–227° C. |
| 24 | " | " | 4-CN | " | mp 198°–200° C. |
| 25 | " | " | 2,4-$Cl_2$ | " | mp 190°–192° C. |
| 26 | " | " | 2-Cl, 4-$NO_2$ | " | mp 189°–191° C. |

Table 1-continued

Structure:

X₁–N=... pyrazole ring with N-X₂, bearing –CO–C₆H₄–(Y)ₗ and –OZ substituents

| Compound No. | X₁ | X₂ | (Y)ₗ | Z | Physical constant |
|---|---|---|---|---|---|
| 27 | " | " | 2,4-Cl₂ | –CH₂CO–(2-thienyl) | mp 74°–77° C. |
| 28 | " | " | " | –CH₂CO–(5-methyl-2-thienyl) | mp 50°–52° C. |
| 29 | " | " | " | (5-chloro-2-thienyl) | mp 74°–76° C. |
| 30 | " | " | " | –CH₂CO–(2,5-dichloro-3-thienyl) | mp 196°–199° C. |
| 31 | " | " | 2-Cl, 4-NO₂ | –CH₂CO–(5-methyl-2-thienyl) | mp 122°–124° C. |
| 32 | " | " | 2-Cl | –CH₂CO–C₆H₅ | mp 128°–129° C. |
| 33 | " | " | " | –CH₂CO–C₆H₄–4-CH₃ | pale yellow oil |
| 34 | " | " | 2-NO₂ | –CH₂CO–C₆H₅ | mp 115°–120° C. |
| 35 | " | " | " | –CH₂CO–C₆H₄–4-CH₃ | brown oil |
| 36 | " | " | 4-CN | –CH₂CO–C₆H₅ | brown oil |
| 37 | " | " | 4-CN | –CH₂CO–C₆H₄–4-CH₃ | brown oil * |
| 38 | " | " | 2,4-Cl₂ | –CH₂CO–C₆H₅ | mp 102°–104° C. |
| 39 | " | " | " | –CH₂CO–C₆H₄–4-Cl | brown oil * |

Table 1-continued

[Structure: X₁—C(=N—N(X₂))—C(=C(OZ))—CO—C₆H₄—(Y)ₗ pyrazole core with aryloxy/ester]

| Compound No. | X₁ | X₂ | (Y)ₗ | Z | Physical constant |
|---|---|---|---|---|---|
| 40 | " | " | " | —CH₂CO—(2,4-diCl-C₆H₃) | brown oil |
| 41 | " | " | " | —CH₂CO—(4-NO₂-C₆H₄) | mp 74°–75° C. |
| 42 | " | " | " | —CH₂CO—(2,4-diNO₂-C₆H₃) | mp |
| 43 | " | " | " | —CH₂CO—(2-CH₃-C₆H₄) | mp 84°–86° C. |
| 44 | " | " | " | —CH₂CO—(3-CH₃-C₆H₄) | mp 76°–78° C. |
| 45 | " | " | " | —CH₂CO—(4-CH₃-C₆H₄) | brown oil * |
| 46 | " | C₂H₅ | " | " | |
| 47 | " | CH₃ | " | —CH₂CO—(2,4-diCH₃-C₆H₃) | brown oil |
| 48 | " | " | " | —CH₂CO—(2,5-diCH₃-C₆H₃) | brown oil |
| 49 | " | " | " | —CH₂CO—(2,4,5-triCH₃-C₆H₂) | brown oil |
| 50 | " | " | " | —CH₂CO—(4-C₂H₅-C₆H₄) | |

Table 1-continued
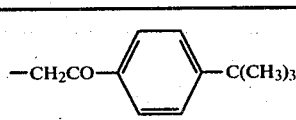
| Compound No. | X₁ | X₂ | (Y)ₗ | Z | Physical constant |
|---|---|---|---|---|---|
| 51 | " | " | " | 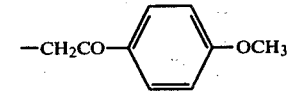 | brown oil |
| 52 | " | " | " | 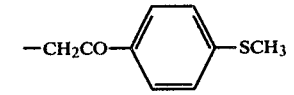 | brown oil |
| 53 | " | " | " | 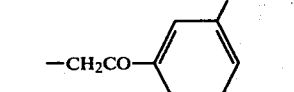 | brown oil * |
| 54 | " | " | " | 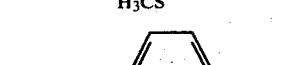 | brown oil |
| 55 | " | " | " | 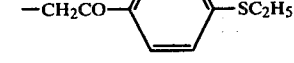 | brown oil * |
| 56 | " | " | " | 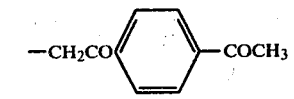 | pale yellow oil |
| 57 | " | " | " | 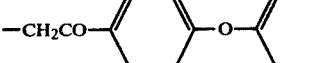 | brown oil |
| 58 | " | " | " | 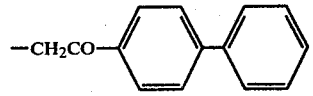 | brown oil |
| 59 | " | " | " | 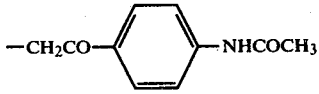 | brown oil |
| 60 | " | " | " | 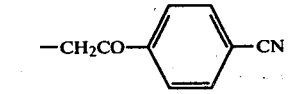 | |
| 61 | " | " | " | 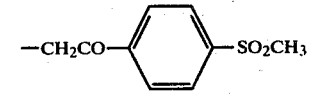 | mp 133°–134° C. |
| 62 | " | " | " | 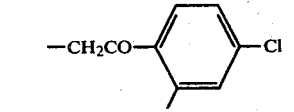 | |
| 63 | " | " | 2-Cl, 4-NO₂ |  | brown oil |

Table 1-continued

Structure:

$X_1$ on pyrazole ring with CO-phenyl-$(Y)_l$ group, OZ substituent, and $X_2$ on N.

| Compound No. | $X_1$ | $X_2$ | $(Y)_l$ | Z | Physical constant |
|---|---|---|---|---|---|
| 64 | " | " | 2-Cl, 4-NO$_2$ | —CH$_2$CO—C$_6$H$_4$—CH$_3$ | brown oil |
| 65 | " | " | 2-Cl, 4-NO$_2$ | —CH$_2$CO—(phenyl with CH$_3$ and H$_3$CS) | mp 50.5°–52.5° C. |
| 66 | " | " | 2-NO$_2$, 4-Cl | —CH$_2$CO—C$_6$H$_5$ | yellow oil |
| 67 | " | " | 2-NO$_2$, 4-Cl | —CH$_2$CO—C$_6$H$_4$—CH$_3$ | brown oil |
| 68 | " | " | 2,4-(NO$_2$)$_2$ | —CH$_2$CO—C$_6$H$_5$ | mp 193°–198° C. |
| 69 | " | " | 3,5-(NO$_2$)$_2$ | —CH$_2$CO—C$_6$H$_4$—CH$_3$ | brown oil |
| 70 | " | " | 2-(—O—C$_6$H$_3$(Cl)(Cl)) | —CH$_2$CO—C$_6$H$_4$—CH$_3$ | brown oil |

*IR spectrum (cm$^{-1}$; KBr)
compound 37  2225, 1685, 1625, 1605, 1510, 1230, 960, 810
compound 39  1700, 1625, 1585, 1505, 1225, 960, 820
compound 45  1690, 1625, 1605, 1505, 1225, 960, 805
compound 53  1685, 1625, 1580, 1505, 1225, 960, 815
compound 55  1690, 1625, 1585, 1510, 1230, 960, 820

The herbicidal experiments and the compositions of the pyrazole derivatives of the present invention will be further described by certain examples.

EXPERIMENT 1

A paddy soil was fed in a pot of 1/2,000 to 1/5,000 are (1/20 to 1/50 m$^2$) and the pot was saturated with water. Seeds of edible barnyard grass were sown and the surface of the pot was covered with a soil in a thin thickness to germinate in an up-land condition. When coleoptiles appeared, the pot was flooded with water in a depth of 3 cm. An aqueous dispersion of each active ingredient was added dropwise at a dose of 100 g of the active ingredient per are (100 g/a). Three weeks after the treatment, the growth condition was visually observed. The inhibition rate was evaluated under the following rating (5 grade rating method). The results are shown in Table 2.

Inhibition rate: 5: complete control
∫
1: no inhibition

Table 2

| Compound No. | Inhibition rate | Compound No. | Inhibition rate | Compound No. | Inhibition rate |
|---|---|---|---|---|---|
| 1 | 4 | 28 | 5 | 48 | 5 |
| 2 | 3 | 29 | 5 | 49 | 5 |
| 3 | 5 | 30 | 5 | 50 | 5 |
| 4 | 4 | 31 | 5 | 51 | 5 |
| 5 | 5 | 32 | 5 | 52 | 5 |
| 6 | 5 | 33 | 5 | 53 | 5 |
| 8 | 3 | 34 | 5 | 54 | 5 |
| 11 | 5 | 35 | 5 | 55 | 5 |
| 15 | 5 | 36 | 5 | 56 | 5 |
| 16 | 5 | 37 | 5 | 57 | 5 |
| 17 | 5 | 38 | 5 | 58 | 5 |

Table 2-continued

| Compound No. | Inhibition rate | Compound No. | Inhibition rate | Compound No. | Inhibition rate |
|---|---|---|---|---|---|
| 18 | 5 | 39 | 5 | 59 | 5 |
| 19 | 3 | 40 | 5 | 61 | 5 |
| 20 | 5 | 41 | 5 | 62 | 5 |
| 21 | 4 | 42 | 5 | 64 | 5 |
| 23 | 5 | 43 | 5 | 65 | 5 |
| 24 | 5 | 44 | 5 | 67 | 5 |
| 25 | 5 | 45 | 5 | 70 | 5 |
| 26 | 5 | 46 | 5 | | |
| 27 | 5 | 47 | 5 | | |

EXPERIMENT 2

In accordance with Experiment 1 except varying the dose of the active ingredient to 2.5, 5 or 10 g/are, the test was repeated. The weeds were drawn out and dried and weighed. Each percentage of the weight of dried weeds to that of the non-treated pot was measured as a percent residual weeds (%).

Table 3

| Compound No. | Percent residual weeds (%) Dose of active ingredient (g/a) | | |
|---|---|---|---|
| | 10 | 5 | 2.5 |
| 38 | 0 | 3 | 16 |
| 43 | 0 | 12 | 21 |
| 45 | 0 | 2 | 5 |
| 1,3-dimethyl-4-(2,4-dichloro-benzoyl)-5-pyrazolyl 4-toluenesulfonate (comparison) | 11 | 72 | 100 |

EXPERIMENT 3

A paddy soil was fed in a pot of 1/2,000 are (1/20 m$^2$), and the pot was saturated with water. Seeds of edible barnyard grass were sown and the surface of the pot was covered with a soil in a thin thickness to germinate in an up-land condition. After the germination, the pot was flooded with water in a depth of 3 cm. When coleoptiles appeared, rice seedlings in 2.5-leaf stage were transplanted. Three days after the transplantation, an aqueous dispersion of each active ingredient was added dropwise to give the specific dose. Four weeks after the treatment, the growth condition was visually observed. The inhibition rate of the barnyard grass was evaluated by the ratings in Experiment 1. Moreover, phytotoxicity of the active ingredient to rice plant was tested. The results are shown in Table 4.

Table 4

| Compound No. | Dose of active ingredient (g/a) | Inhibition rate of barnyard grass | Phytotoxicity of rice plant |
|---|---|---|---|
| | 45 | 5 | None |
| 25 | 30 | 5 | None |
| | 15 | 5 | None |
| | 45 | 5 | None |
| 38 | 30 | 5 | None |
| | 15 | 5 | None |
| | 45 | 5 | None |
| 43 | 30 | 5 | None |
| | 15 | 5 | None |
| | 45 | 5 | None |
| 45 | 30 | 5 | None |
| | 15 | 5 | None |
| | 45 | 5 | None |
| 52 | 30 | 5 | None |
| | 15 | 5 | None |

EXPERIMENT 4

A soil was fed in a pot of 1/5,000 are (1/50 m$^2$) and the pot was flooded with water. Seeds of bulrush were sown and tubers of arrowhead were planted and they were grown in a greenhouse. When bulrush and arrowhead were grown to about 2-leaf stage, the pot was flooded in a depth of 3 cm and an aqueous dispersion of each active ingredient was added dropwise at a dose of 30 g of the active ingredient per are (30 g/a). Three weeks after the treatment, the growth condition was visually observed. The inhibition rates of the weeds were evaluated by the rating in Experiment 1. The results are shown in Table 5.

Table 5

| Compound No. | Inhibition rate | |
|---|---|---|
| | Bulrush | Arrowhead |
| 25 | 5 | 5 |
| 38 | 5 | 5 |
| 43 | 5 | 5 |
| 45 | 5 | 5 |
| 52 | 5 | 4–5 |
| 1,3-dimethyl-4-(3-nitrobenzoyl)-5-hydroxy pyrazole (comparison) | 1 | 1 |

Composition 1

Bentonite: 58 wt. parts
Jeeklite (principal component; kaolinite): 30 wt. parts
Sodium lignin sulfonte: 5 wt. parts The components were mixed and granulated. A solution prepared by diluting 7 wt. parts of 1,3-dimethyl-4-(2,4-dichlorobenzoyl)-5-(4-methylbenzoylmethoxy) pyrazole with suitable amount of acetone was sprayed onto the granules to obtain granule.

Composition 2

1,3-Dimethyl-4-(2,4-dichlorobenzoyl)-5-(benzoylmethoxy) pyrazole: 10 wt. parts
Bentonite: 85 wt. parts
Sodium lignin sulfonate: 5 wt. parts The components were uniformly mixed and suitable amount of water was added and the mixture was granulated to obtain granule.

Composition 3

1,3-Dimethyl-4-(2-nitro-4-chlorobenzoyl)-5-(4-methylbenzoylmethoxy) pyrazole: 20 wt. parts
Jeeklite: 75 wt. parts
Sodium naphthalenesulfonate-formaldehyde condensate: 2 wt. parts
Sodium lignin sulfonate: 3 wt. parts The components were uniformly mixed to obtain a wettable powder.

Composition 4

Jeeklite: 78 wt. parts
Sodium naphthalenesulfonate-formaldehyde condensate: 2 wt. parts
Sulfate of polyoxyethylene alkylaryl ether: 5 wt. parts
Fine silicon dioxide (SiO$_2$.nH$_2$O): 15 wt. parts The mixture of the components were mixed with 1,3-dimethyl-4-(2,4-dichlorobenzoyl)-5-(4-methoxybenzoylmethoxy) pyrazole at a ratio of 4:1 by weight to obtain a wettable powder.

Composition 5

1,3-Dimethyl-4-(2,4-dichlorobenzoyl)-5-(2,4-dinitrophenoxy) pyrazole: 20 wt. parts
Xylene: 60 wt. parts
Polyoxyethylene stearate: 20 wt. parts
The components were uniformly mixed to obtain an emulsifiable concentrate.

Composition 6

1,3-Dimethyl-4-(2,4-dichlorobenzoyl)-5-(benzoylmethoxy) pyrazole: 10 wt. parts
Jeeklite: 25 wt. parts
Polyethyleneglycol oleyl ether: 1 wt. parts
Fine silicon dioxide ($SiO_2.nH_2O$): 1 wt. parts
The components were blended and fined to obtain the mixture (I).
Sodium tripolyphosphate: 3 wt. parts
Sodium lignin sulfonate: 2 wt. parts
Sodium dodecylbenzene sulfonate: 2 wt. parts
Bentonite: 56 wt. parts
The components were blended and fined to obtain the mixture (II).
These mixture (I) and (II) were blended, fined and granulated to obtain granule.

Composition 7

1,3-Dimethyl-4-(2,4-dichlorobenzoyl)-5-(4-methylbenzoylmethoxy) pyrazole: 10 wt. parts
Polyethyleneglycol dodecylphenyl ether: 2 wt. parts
The components were blended and fined to obtain the mixture (I).
Bentonite: 57 wt. parts
Jeeklite: 25 wt. parts
Mixture of alkylaryl sulfonate and polyoxyethylene alkyl phosphate: 6 wt. parts
The components were blended and fined to obtain the mixture (II).
These mixture (I) and (II) were blended, fined and granulated to obtain granule.

As it is clearly understood from the results of the above-mentioned experiments, the pyrazole derivatives of the present invention impart excellent herbicidal effect. In the paddy field, annual weeds such as barnyard grass, false pimpernel (*Lindernia procumbens* PHILCOX), wavy bittercress (*Cardamine flexuosa* WITH) and toothcup as well as perennial weeds such as bulrush, water nutgrass (*Cyperus serotinus* ROTTB), water plantain and arrowhead which have not been easily controlled with the conventional herbicides, can be effectively controlled by an application in a post- or pre-emergence of weeds.

The herbicidal activity to the annual weeds is superior to the conventional pyrazole herbicidal compounds at the initial stage of growth of the weeds.

Since no phytotoxicity to rice plants is caused at a dose sufficient to completely control the weeds, the pyrazole derivatives of the present invention can be used as a herbicide in safety.

On the other hand, in an up-land, the pyrazole derivatives of the present invention are effective to control noxious weeds without any phytotoxicity to useful plants by a soil treatment at about emergence of the noxious weeds.

Certain compounds of the pyrazole derivatives of the present invention impart insecticidal effect to plant parasitic mites such as carmine mite (*Tetranychus telarius* Linné) and two-spotted spider mite (*Tetranychus urticae* Koch).

The pyrazole derivatives of the present invention impart excellent herbicidal activity to various weeds and can be applied to various places such as paddy fields as well as up-lands, orchards, mulberry farms, forests, ridges, grounds and factory sites. They can be applied by a soil treatment and a foliar treatment.

The pyrazole derivatives of the present invention can be mixed with various adjuvants in accordance with the known preparations of agricultural compositions to prepare compositions such as an emulsifiable concentrate, a wettable powder, a dust and a granule.

The adjuvants include solid carriers such as diatomaceous earth, slaked lime, calcium carbonate, talc, fine silicon dioxide, kaolin, bentonite, jeeklite, vermiculite and sand; solvents such as benzene, toluene, xylene, solvent naphtha, ethanol, dioxane, isophorone, methyl ethyl ketone, methyl isobutyl ketone, dimethylformamide, dimethylsulfoxide, N-methylpyrrolidone and water and optionally anionic or nonionic surfactants such as sodium alkylsulfate, sodium alkylbenzenesulfonate, sodium lignin sulfonate, polyoxyethylene lauryl ether, polyoxyethylene alkylaryl ether, polyoxyethylene fatty acid ester, polyoxyethylene sorbitan fatty acid ester, sodium naphthalenesulfonate-formaldehyde condensate, sulfate of polyoxyethylene alkylaryl ether, polyethyleneglycol oleyl ether, and polyethyleneglycol dodecylphenyl ether, and further optionally bilders such as sodium carbonate, potassium carbonate, sodium tripolyphosphate, sodium metasilicate, and binders such as polyvinyl alcohol, carboxymethylcellulose, arabic gum, starch, casein.

The ratios of the components in the composition are dependent upon the forms of the compositions.

|  | Usual ratio (wt. %) | Preferable ratio (wt. %) |
| --- | --- | --- |
| Active ingredient | 1 to 90 | 1 to 70 |
| Carrier or solvent | 5 to 99 | 25 to 99 |
| Surfactant | 0 to 30 | 1 to 20 |

Further, the ratios of the components in the each composition are illustrated bellow.
Granule:
Active ingredient: 1 to 30 wt. %
Carrier: 60 to 99 wt. %
Surfactant: 0 to 15 wt. %
Wettable powder:
Active ingredient: 20 to 85 wt. %
Carrier: 5 to 75 wt. %
Surfactant: 5 to 10 wt. %
Dust:
Active ingredient: 3 to 20 wt. %
Carrier: 75 to 97 wt. %
Surfactant: 0 to 5 wt. %
Emulsifiable concentrate:
Active ingredient: 10 to 50 wt. %
Solvent: 25 to 80 wt. %
Surfactant: 10 to 30 wt. %

The pyrazole derivative of the present invention can be used with the other agricultural chemicals such as the other herbicides, insecticides and fungicides; and fertilizers and soils. Synergism may be imparted in certain combinations.

The doses of the pyrazole derivative of the present invention vary depending upon such conditions as the weather, the soil, the form of the composition, the season, the method of application and the type of weeds treated. The dose of the active ingredient is usually in a range of 1 to 500 g per are, preferably 10 to 100 g per are.

Although certain preparations of the compounds, herbicidal experiments of the compounds and compositions of the compounds are described as the examples, it will be apparent to one of ordinary skill in the art that many changes and modifications can be made thereto without departing from the scope of the invention as set forth herein.

What is claimed is:

1. A pyrazole derivative having the formula:

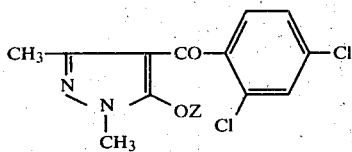

wherein Z is

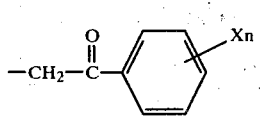

group (wherein X is a ($C_1$–$C_4$) alkyl group or a ($C_1$–$C_4$) alkylthio group, and n is 0, 1 or 2).

2. The pyrazole derivative of claim 1 having the formula:

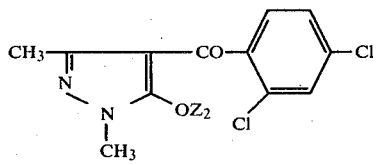

wherein $Z_2$ is selected from the group consisting of:

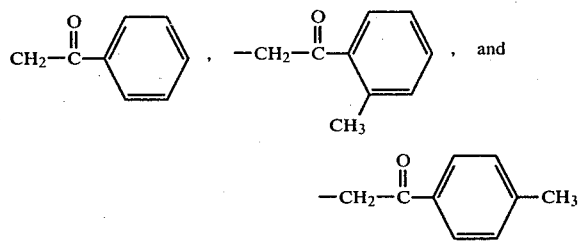

3. The pyrazole derivative according to claim 1, wherein the compound is 1,3-dimethyl-4-(2,4-dichlorobenzoyl)-5-(benzoylmethoxy) pyrazole.

4. The pyrazole derivative according to claim 1, wherein the compound is 1,3-dimethyl-4-(2,4-dichlorobenzoyl)-5-(2-methylbenzoylmethoxy) pyrazole.

5. The pyrazole derivative according to claim 1, wherein the compound is 1,3-dimethyl-4-(2,4-dichlorobenzoyl)-5-(3-methylbenzoylmethoxy) pyrazole.

6. The pyrazole derivative according to claim 1, wherein the compound is 1,3-dimethyl-4-(2,4-dichlorobenzoyl)-5-(4-methylbenzoylmethoxy) pyrazole.

7. A herbicidal composition comprising a herbicidally effective amount of at least one compound having the formula:

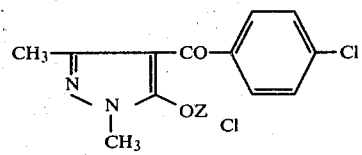

where in Z is

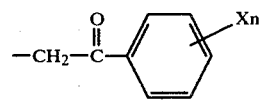

group (wherein X is a ($C_1$–$C_4$) alkyl group or a ($C_1$–$C_4$) alkylthio group, and n is 0, 1 or 2) as an active ingredient, and an agricultually acceptable adjuvant.

8. The herbicidal composition of claim 7, wherein the compound has the formula:

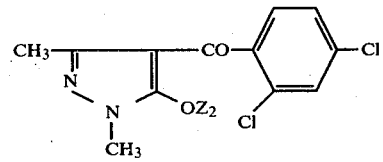

wherein $Z_2$ is selected from the group consisting of:

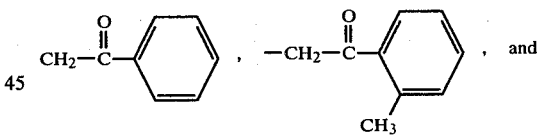

9. The herbicidal composition according to claim 7, wherein the compound is 1,3-dimethyl-4-(2,4-dichlorobenzoyl)-5-(benzoylmethoxy) pyrazole.

10. The herbicidal composition according to claim 7, wherein the compound is 1,3-dimethyl-4-(2,4-dichlorobenzoyl)-5-(2-methylbenzoylmethoxy) pyrazole.

11. The herbicidal composition according to claim 7, wherein the compound is 1,3-dimethyl-4-(2,4-dichlorobenzoyl)-5-(3-methylbenzoylmethoxy) pyrazole.

12. The herbicidal composition according to claim 7, wherein the compound is 1,3-dimethyl-4-(2,4-dichlorobenzoyl)-5-(4-methylbenzoylmethoxy) pyrazole.

* * * * *